US011589621B2

(12) United States Patent
Sur et al.

(10) Patent No.: US 11,589,621 B2
(45) Date of Patent: *Feb. 28, 2023

(54) HEART RATE MONITOR FOR AN AEROSOL DELIVERY DEVICE

(71) Applicant: RAI STRATEGIC HOLDINGS, INC., Winston-Salem, NC (US)

(72) Inventors: Rajesh Sur, Winston-Salem, NC (US); Sawyer A. Hubbard, Winston-Salem, NC (US); Kyung Soo Hong, Clemmons, NC (US); Stephen B. Sears, Siler City, NC (US)

(73) Assignee: RAI Strategic Holdings, Inc., Winston-Salem, NC (US)

(*) Notice: Subject to any disclaimer, the term of this patent is extended or adjusted under 35 U.S.C. 154(b) by 341 days.

This patent is subject to a terminal disclaimer.

(21) Appl. No.: 16/730,201

(22) Filed: Dec. 30, 2019

(65) Prior Publication Data

US 2020/0128877 A1 Apr. 30, 2020

Related U.S. Application Data

(63) Continuation-in-part of application No. 15/602,932, filed on May 23, 2017, now Pat. No. 10,517,330.

(51) Int. Cl.
*A24F 40/49* (2020.01)
*A24F 40/51* (2020.01)
(Continued)

(52) U.S. Cl.
CPC .............. *A24F 40/49* (2020.01); *A24F 40/51* (2020.01); *A24F 40/65* (2020.01); *A61M 15/06* (2013.01);
(Continued)

(58) Field of Classification Search
None
See application file for complete search history.

(56) References Cited

U.S. PATENT DOCUMENTS

| 1,514,682 A | 11/1924 | Wilson |
| 1,771,366 A | 7/1930 | Wyss et al. |

(Continued)

FOREIGN PATENT DOCUMENTS

| AU | 276250 | 7/1965 |
| CA | 2 641 869 | 5/2010 |

(Continued)

OTHER PUBLICATIONS

International Search Report in the corresponding International Application No. PCT/IB2020/062496 dated Feb. 16, 2021, 6 pages.

(Continued)

*Primary Examiner* — Thor S Campbell
(74) *Attorney, Agent, or Firm* — Womble Bond Dickinson (US) LLP

(57) ABSTRACT

An aerosol delivery device is provided that includes at least one housing structured to retain an aerosol precursor composition. The device includes an atomizer, and a microprocessor configured to operate in an active mode in which the control body is configured to control the atomizer to activate and produce an aerosol from the aerosol precursor composition. And the device includes a heart rate monitor including a plurality of biopotential electrodes affixed to the housing and configured to obtain biopotential measurements from a user, and including signal conditioning circuitry configured to produce an electrocardiogram signal from the biopotential measurements. The microprocessor is coupled to the signal conditioning circuitry and further configured to control operation of at least one functional element of the aerosol (Continued)

delivery device based on the electrocardiogram signal or a heart rate of the user calculated therefrom.

22 Claims, 3 Drawing Sheets

(51) Int. Cl.
    *A24F 40/65* (2020.01)
    *A61M 15/06* (2006.01)
(52) U.S. Cl.
    CPC ... *A61M 2205/35* (2013.01); *A61M 2205/609* (2013.01); *A61M 2230/04* (2013.01)

(56) References Cited

U.S. PATENT DOCUMENTS

| | | | |
|---|---|---|---|
| 2,057,353 A | 10/1936 | Whittemore, Jr. | |
| 2,104,266 A | 1/1938 | McCormick | |
| 3,200,819 A | 8/1965 | Gilbert | |
| 3,479,561 A | 11/1969 | Janning | |
| 4,120,294 A | 10/1978 | Wolfe | |
| 4,270,547 A | 6/1981 | Steffen et al. | |
| 4,284,089 A | 8/1981 | Ray | |
| 4,303,083 A | 12/1981 | Burruss, Jr. | |
| 4,735,217 A | 4/1988 | Gerth et al. | |
| 4,848,374 A | 7/1989 | Chard et al. | |
| 4,907,606 A | 3/1990 | Lilja et al. | |
| 4,922,901 A | 5/1990 | Brooks et al. | |
| 4,945,931 A | 8/1990 | Gori | |
| 4,947,874 A | 8/1990 | Brooks et al. | |
| 4,947,875 A | 8/1990 | Brooks et al. | |
| 4,986,286 A | 1/1991 | Roberts et al. | |
| 5,019,122 A | 5/1991 | Clearman et al. | |
| 5,042,510 A | 8/1991 | Curtiss et al. | |
| 5,060,671 A | 10/1991 | Counts et al. | |
| 5,093,894 A | 3/1992 | Deevi et al. | |
| 5,144,962 A | 9/1992 | Counts et al. | |
| 5,249,586 A | 10/1993 | Morgan et al. | |
| 5,261,424 A | 11/1993 | Sprinkel, Jr. | |
| 5,322,075 A | 6/1994 | Deevi et al. | |
| 5,353,813 A | 10/1994 | Deevi et al. | |
| 5,369,723 A | 11/1994 | Counts et al. | |
| 5,372,148 A | 12/1994 | McCafferty et al. | |
| 5,388,574 A | 2/1995 | Ingebrethsen et al. | |
| 5,408,574 A | 4/1995 | Deevi et al. | |
| 5,468,936 A | 11/1995 | Deevi et al. | |
| 5,498,850 A | 3/1996 | Das | |
| 5,515,842 A | 5/1996 | Ramseyer et al. | |
| 5,530,225 A | 6/1996 | Hajaligol | |
| 5,564,442 A | 10/1996 | MacDonald et al. | |
| 5,602,932 A | 2/1997 | Macdonald et al. | |
| 5,649,554 A | 7/1997 | Sprinkel et al. | |
| 5,666,977 A | 9/1997 | Higgins et al. | |
| 5,687,746 A | 11/1997 | Rose et al. | |
| 5,726,421 A | 3/1998 | Fleischhauer et al. | |
| 5,727,571 A | 3/1998 | Meiring et al. | |
| 5,743,251 A | 4/1998 | Howell et al. | |
| 5,799,663 A | 9/1998 | Gross et al. | |
| 5,819,756 A | 10/1998 | Mielordt | |
| 5,865,185 A | 2/1999 | Collins et al. | |
| 5,865,186 A | 2/1999 | Volsey, II | |
| 5,878,752 A | 3/1999 | Adams et al. | |
| 5,894,841 A | 4/1999 | Voges | |
| 5,934,289 A | 8/1999 | Watkins et al. | |
| 5,954,979 A | 9/1999 | Counts et al. | |
| 5,967,148 A | 10/1999 | Harris et al. | |
| 6,040,560 A | 3/2000 | Fleischhauer et al. | |
| 6,053,176 A | 4/2000 | Adams et al. | |
| 6,089,857 A | 7/2000 | Matsuura et al. | |
| 6,095,153 A | 8/2000 | Kessler et al. | |
| 6,125,853 A | 10/2000 | Susa et al. | |
| 6,155,268 A | 12/2000 | Takeuchi | |
| 6,164,287 A | 12/2000 | White | |
| 6,196,218 B1 | 3/2001 | Voges | |
| 6,196,219 B1 | 3/2001 | Hess et al. | |
| 6,598,607 B2 | 7/2003 | Adiga et al. | |
| 6,601,776 B1 | 8/2003 | Oljaca et al. | |
| 6,615,840 B1 | 9/2003 | Fournier et al. | |
| 6,688,313 B2 | 2/2004 | Wrenn et al. | |
| 6,772,756 B2 | 8/2004 | Shayan | |
| 6,803,545 B2 | 10/2004 | Blake et al. | |
| 6,854,461 B2 | 2/2005 | Nichols | |
| 6,854,470 B1 | 2/2005 | Pu | |
| 7,117,867 B2 | 10/2006 | Cox et al. | |
| 7,293,565 B2 | 11/2007 | Griffin et al. | |
| 7,513,253 B2 | 4/2009 | Kobayashi et al. | |
| 7,775,459 B2 | 8/2010 | Martens, III et al. | |
| 7,832,410 B2 | 11/2010 | Hon | |
| 7,845,359 B2 | 12/2010 | Montaser | |
| 7,896,006 B2 | 3/2011 | Hamano et al. | |
| 8,127,772 B2 | 3/2012 | Montaser | |
| 8,314,591 B2 | 11/2012 | Terry et al. | |
| 8,365,742 B2 | 2/2013 | Hon | |
| 8,402,976 B2 | 3/2013 | Fernando et al. | |
| 8,499,766 B1 | 8/2013 | Newton | |
| 8,528,569 B1 | 9/2013 | Newton | |
| 8,550,069 B2 | 10/2013 | Alelov | |
| 8,851,081 B2 | 10/2014 | Fernando et al. | |
| 9,603,386 B2 * | 3/2017 | Xiang | A24F 40/50 |
| 9,675,114 B2 | 6/2017 | Timmermans | |
| 2002/0146242 A1 | 10/2002 | Vieira | |
| 2003/0226837 A1 | 12/2003 | Blake et al. | |
| 2004/0118401 A1 | 6/2004 | Smith et al. | |
| 2004/0129280 A1 | 7/2004 | Woodson et al. | |
| 2004/0200488 A1 | 10/2004 | Felter et al. | |
| 2004/0226568 A1 | 11/2004 | Takeuchi et al. | |
| 2005/0016550 A1 | 1/2005 | Katase | |
| 2006/0016453 A1 | 1/2006 | Kim | |
| 2006/0196518 A1 | 9/2006 | Hon | |
| 2007/0074734 A1 | 4/2007 | Braunshteyn et al. | |
| 2007/0102013 A1 | 5/2007 | Adams et al. | |
| 2007/0215167 A1 | 9/2007 | Crooks et al. | |
| 2008/0085103 A1 | 4/2008 | Beland et al. | |
| 2008/0092912 A1 | 4/2008 | Robinson et al. | |
| 2008/0257367 A1 | 10/2008 | Paterno et al. | |
| 2008/0276947 A1 | 11/2008 | Martzel | |
| 2008/0302374 A1 | 12/2008 | Wengert et al. | |
| 2009/0095311 A1 | 4/2009 | Hon | |
| 2009/0095312 A1 | 4/2009 | Heibrich et al. | |
| 2009/0126745 A1 | 5/2009 | Hon | |
| 2009/0188490 A1 | 7/2009 | Hon | |
| 2009/0230117 A1 | 9/2009 | Fernando et al. | |
| 2009/0272379 A1 | 11/2009 | Thorens et al. | |
| 2009/0283103 A1 | 11/2009 | Nielsen et al. | |
| 2009/0312656 A1 * | 12/2009 | Lau | A61B 5/02444 600/509 |
| 2009/0320863 A1 | 12/2009 | Fernando et al. | |
| 2010/0043809 A1 | 2/2010 | Magnon | |
| 2010/0083959 A1 | 4/2010 | Siller | |
| 2010/0200006 A1 | 8/2010 | Robinson et al. | |
| 2010/0229881 A1 | 9/2010 | Hearn | |
| 2010/0242974 A1 | 9/2010 | Pan | |
| 2010/0307518 A1 | 12/2010 | Wang | |
| 2010/0313901 A1 | 12/2010 | Fernando et al. | |
| 2011/0005535 A1 | 1/2011 | Xiu | |
| 2011/0011396 A1 | 1/2011 | Fang | |
| 2011/0036363 A1 | 2/2011 | Urtsev et al. | |
| 2011/0036365 A1 | 2/2011 | Chong et al. | |
| 2011/0094523 A1 | 4/2011 | Thorens et al. | |
| 2011/0126848 A1 | 6/2011 | Zuber et al. | |
| 2011/0155153 A1 | 6/2011 | Thorens et al. | |
| 2011/0155718 A1 | 6/2011 | Greim et al. | |
| 2011/0168194 A1 | 7/2011 | Hon | |
| 2011/0265806 A1 | 11/2011 | Alarcon et al. | |
| 2011/0309157 A1 | 12/2011 | Yang et al. | |
| 2012/0042885 A1 | 2/2012 | Stone et al. | |
| 2012/0060853 A1 | 3/2012 | Robinson et al. | |
| 2012/0090630 A1 * | 4/2012 | Hon | A24B 15/167 131/273 |
| 2012/0111347 A1 | 5/2012 | Hon | |
| 2012/0132643 A1 | 5/2012 | Choi et al. | |
| 2012/0172684 A1 * | 7/2012 | Buchheim | A61B 5/02438 600/301 |

(56) References Cited

U.S. PATENT DOCUMENTS

| | | |
|---|---|---|
| 2012/0227752 A1 | 9/2012 | Alelov |
| 2012/0231464 A1 | 9/2012 | Yu et al. |
| 2012/0260927 A1 | 10/2012 | Liu |
| 2012/0279512 A1 | 11/2012 | Hon |
| 2012/0318882 A1 | 12/2012 | Abehasera |
| 2013/0037041 A1 | 2/2013 | Worm et al. |
| 2013/0056013 A1 | 3/2013 | Terry et al. |
| 2013/0081625 A1 | 4/2013 | Rustad et al. |
| 2013/0081642 A1 | 4/2013 | Safari |
| 2013/0192619 A1 | 8/2013 | Tucker et al. |
| 2013/0220315 A1* | 8/2013 | Conley ............... H05B 1/0244 128/202.21 |
| 2013/0255702 A1 | 10/2013 | Griffith, Jr. et al. |
| 2013/0303922 A1* | 11/2013 | Buchheim ............ A61B 5/11 600/479 |
| 2013/0306084 A1 | 11/2013 | Flick |
| 2013/0319439 A1 | 12/2013 | Gorelick et al. |
| 2013/0340750 A1 | 12/2013 | Thorens et al. |
| 2013/0340775 A1 | 12/2013 | Juster et al. |
| 2014/0000638 A1 | 1/2014 | Sebastian et al. |
| 2014/0018635 A1* | 1/2014 | Buchheim ........... A61B 5/7221 600/301 |
| 2014/0060554 A1* | 3/2014 | Collett ................ A24F 40/30 392/386 |
| 2014/0060555 A1 | 3/2014 | Chang et al. |
| 2014/0096781 A1 | 4/2014 | Sears et al. |
| 2014/0096782 A1 | 4/2014 | Ampolini et al. |
| 2014/0109921 A1 | 4/2014 | Chen |
| 2014/0157583 A1 | 6/2014 | Ward et al. |
| 2014/0190496 A1 | 7/2014 | Wensley et al. |
| 2014/0209105 A1 | 7/2014 | Sears et al. |
| 2014/0253144 A1 | 9/2014 | Novak et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0261495 A1 | 9/2014 | Novak et al. |
| 2014/0270727 A1 | 9/2014 | Ampolini et al. |
| 2014/0270729 A1 | 9/2014 | DePiano et al. |
| 2014/0270730 A1 | 9/2014 | DePiano et al. |
| 2014/0345631 A1* | 11/2014 | Bowen ................ A61P 25/26 131/328 |
| 2015/0007838 A1 | 1/2015 | Fernando et al. |
| 2015/0053217 A1 | 2/2015 | Steingraber et al. |
| 2015/0122252 A1 | 5/2015 | Frija |
| 2015/0257647 A1* | 9/2015 | Buck ................... A61B 5/6804 600/509 |
| 2016/0037826 A1 | 2/2016 | Hearn et al. |
| 2016/0058074 A1* | 3/2016 | Liu ..................... A24F 40/50 131/329 |
| 2016/0066808 A1* | 3/2016 | Hijazi ................. A61B 5/333 600/382 |
| 2017/0020192 A1* | 1/2017 | Fregonese ........... A24F 40/485 |
| 2017/0136301 A1 | 5/2017 | Cameron |
| 2017/0340209 A1* | 11/2017 | Klaassen ............ A61B 5/021 |
| 2019/0053540 A1* | 2/2019 | Baker ................. A61M 15/002 |
| 2019/0175846 A1 | 6/2019 | Terry et al. |

FOREIGN PATENT DOCUMENTS

| | | |
|---|---|---|
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| CN | 202699101 U | 1/2013 |
| CN | 203952429 U | 11/2014 |
| CN | 105125222 A | 12/2015 |
| CN | 206025207 U | 3/2017 |
| DE | 3438668 A1 | 5/1985 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 2 316 286 | 5/2011 |
| ES | 2370725 A1 | 12/2011 |
| GB | 2 390 429 A | 7/2004 |
| GB | 2469850 | 11/2010 |
| JP | H06339468 A | 12/1994 |
| JP | 2001258857 A | 9/2001 |
| JP | 2016531705 A | 10/2016 |
| JP | 2018-536388 A | 12/2018 |
| RU | 2337720 C2 | 11/2008 |
| WO | WO 1997/48293 | 12/1997 |
| WO | WO 2003/034847 | 5/2003 |
| WO | WO 2004/043175 | 5/2004 |
| WO | WO 2004/080216 | 9/2004 |
| WO | WO 2005/099494 | 10/2005 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/118644 | 10/2010 |
| WO | WO 2010/140937 | 12/2010 |
| WO | WO 2011/010334 | 1/2011 |
| WO | WO 2012/072762 | 6/2012 |
| WO | WO 2012/100523 | 8/2012 |
| WO | WO 2013/089551 | 6/2013 |
| WO | 2017/055795 A1 | 4/2017 |
| WO | 2018/024155 A1 | 2/2018 |
| WO | 2018/205908 A1 | 11/2018 |
| WO | 2018/215939 A1 | 11/2018 |
| WO | WO2017055795 | 2/2019 |

OTHER PUBLICATIONS

Analog Devices, "50µA, 2 mm x 1.7 mm WLCSP, Low Noise, Heart Rate Monitor for Wearable Products", AD8233 Data Sheet, p. 1-30, Created Aug. 9, 2016.

International Search Report dated Aug. 21, 2018 in corresponding International application No. PCT/IB2018/053628 filed May 22, 2018.

Etherington, "Bionym Raises $14M Series A For Its Heartbeat Authentication Wristband", TechCrunch, Sep. 2014, retrieved from https://techcrunch.com/2014/09/24/bionym-raises-14m-series-a-for-its-heartbeat-authentication-wristband/, pp. 1-8.

Diep, "With Nymi Wristband, Your Heartbeat Unlocks Your Devices", Popular Science, Sep. 2013, pp. 1-8.

"Discover", Nymi Enterprise Edition, 2019, pp. 1-3.

* cited by examiner

FIG. 3

HEART RATE MONITOR FOR AN AEROSOL DELIVERY DEVICE

CROSS-REFERENCE TO RELATED APPLICATION(S)

The present application is a continuation-in-part of U.S. patent application Ser. No. 15/602,932, entitled: A Heart Rate Monitor for an Aerosol Delivery Device, filed on May 23, 2017, now U.S. Pat. No. 10,517,330, the content of which is incorporated herein by reference.

TECHNOLOGICAL FIELD

The present disclosure relates to aerosol delivery devices such as smoking articles, and more particularly to aerosol delivery devices that may utilize electrically generated heat for the production of aerosol (e.g., smoking articles commonly referred to as electronic cigarettes). The smoking articles may be configured to heat an aerosol precursor, which may incorporate materials that may be made or derived from, or otherwise incorporate tobacco, the precursor being capable of forming an inhalable substance for human consumption.

BACKGROUND

Many devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous alternative smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 8,881,737 to Collett et al., U.S. Pat. App. Pub. No. 2013/0255702 to Griffith Jr. et al., U.S. Pat. App. Pub. No. 2014/0000638 to Sebastian et al., U.S. Pat. App. Pub. No. 2014/0096781 to Sears et al., U.S. Pat. App. Pub. No. 2014/0096782 to Ampolini et al., U.S. Pat. App. Pub. No. 2015/0059780 to Davis et al., and U.S. patent application Ser. No. 15/222,615 to Watson et al., filed Jul. 28, 2016, all of which are incorporated herein by reference. See also, for example, the various implementations of products and heating configurations described in the background sections of U.S. Pat. No. 5,388,594 to Counts et al. and U.S. Pat. No. 8,079,371 to Robinson et al., which are incorporated by reference.

However, it may be desirable to provide aerosol delivery devices with improved electronics such as may extend usability of the devices.

BRIEF SUMMARY

The present disclosure relates to aerosol delivery devices, methods of forming such devices, and elements of such devices. The present disclosure includes, without limitation, the following example implementations.

Some example implementations provide an aerosol delivery device comprising at least one housing structured to retain an aerosol precursor composition; an atomizer; a microprocessor configured to operate in an active mode in which the control body is configured to control the atomizer to activate and produce an aerosol from the aerosol precursor composition; and a heart rate monitor including a plurality of biopotential electrodes affixed to the housing and configured to obtain biopotential measurements from a user, and including signal conditioning circuitry configured to produce an electrocardiogram signal from the biopotential measurements, wherein the microprocessor is coupled to the signal conditioning circuitry and further configured to control operation of at least one functional element of the aerosol delivery device based on the electrocardiogram signal or a heart rate of the user calculated therefrom.

In some example implementations of the aerosol delivery device of any preceding example implementation, or any combination of any preceding example implementations, the electrocardiogram signal or samples of the electrocardiogram signal form an identifier of the user, and the microprocessor is further configured to perform a biometric authentication of the user based on the identifier, and wherein the microprocessor further configured to control operation of the at least one functional element includes the microprocessor further configured to alter a locked state of the aerosol delivery device based on the biometric authentication.

In some example implementations of the aerosol delivery device of any preceding example implementation, or any combination of any preceding example implementations, the microprocessor further configured to perform the biometric authentication includes the microprocessor further configured to at least access a corresponding identifier of an authorized user; perform a comparison of the identifier with the corresponding identifier; and based on the comparison, verify the user is the authorized user when the identifier and the corresponding identifier match or have at least a threshold similarity.

In some example implementations of the aerosol delivery device of any preceding example implementation, or any combination of any preceding example implementations, the microprocessor is further configured to operate in an enrollment mode to enroll the user for biometric authentication, the microprocessor in the enrollment mode configured to receive a baseline electrocardiogram signal for the user from the heart rate monitor, and generate the corresponding identifier from the baseline electrocardiogram signal.

In some example implementations of the aerosol delivery device of any preceding example implementation, or any combination of any preceding example implementations, the microprocessor is further configured to force re-enrollment of the user, including the microprocessor further configured to repeat the enrollment mode in which the microprocessor is configured to receive an updated baseline electrocardiogram signal for the user, and update the corresponding identifier from the updated baseline electrocardiogram signal.

In some example implementations of the aerosol delivery device of any preceding example implementation, or any combination of any preceding example implementations, the microprocessor further configured to perform the biometric authentication includes the microprocessor further configured to at least access corresponding identifiers of an authorized user, the corresponding identifiers formed from respective baseline electrocardiogram signals for the authorized user; perform a comparison of the identifier with the corresponding identifiers; and based on the comparison, verify the user is the authorized user when the identifier and any of the corresponding identifiers match or have at least a threshold similarity.

In some example implementations of the aerosol delivery device of any preceding example implementation, or any combination of any preceding example implementations, the microprocessor is further configured to operate in an enrollment mode in which the microprocessor is configured to receive the respective baseline electrocardiogram signals from the heart rate monitor, and generate the corresponding identifiers from the respective baseline electrocardiogram signals.

In some example implementations of the aerosol delivery device of any preceding example implementation, or any combination of any preceding example implementations, the microprocessor further configured to perform the biometric authentication includes the microprocessor further configured to at least access corresponding identifiers of authorized users, the corresponding identifiers formed from respective baseline electrocardiogram signals for respective ones of the authorized users; perform a comparison of the identifier with the corresponding identifiers; and based on the comparison, verify the user is one of the authorized users when the identifier and any of the corresponding identifiers match or have at least a threshold similarity.

In some example implementations of the aerosol delivery device of any preceding example implementation, or any combination of any preceding example implementations, the microprocessor is further configured to operate in an enrollment mode in which the microprocessor is configured to receive the respective baseline electrocardiogram signals from the heart rate monitor, and generate the corresponding identifiers from the respective baseline electrocardiogram signals.

In some example implementations of the aerosol delivery device of any preceding example implementation, or any combination of any preceding example implementations, the aerosol delivery device further comprises a communication interface configured to enable communication with a computing device, wherein the microprocessor further configured to control operation of the at least one functional element includes the microprocessor further configured to cause the communication interface to communicate a notification to the computing device when the biometric authentication fails to verify the user is an authorized user.

In some example implementations of the aerosol delivery device of any preceding example implementation, or any combination of any preceding example implementations, the aerosol delivery device further comprises a communication interface configured to enable communication with an age verification system that is configured to perform an age verification of the user, wherein the microprocessor is further configured to alter the locked state of the aerosol delivery device based on the age verification.

Some example implementations provide a control body for an aerosol delivery device, the control body comprising a housing; a microprocessor configured to operate in an active mode in which the microprocessor is configured to control an atomizer to activate and produce an aerosol from an aerosol precursor composition; and a heart rate monitor including a plurality of biopotential electrodes affixed to the housing and configured to obtain biopotential measurements from a user, and including signal conditioning circuitry configured to produce an electrocardiogram signal from the biopotential measurements, wherein the microprocessor is coupled to the signal conditioning circuitry and further configured to control operation of at least one functional element of the control body or the aerosol delivery device based on the electrocardiogram signal or a heart rate of the user calculated therefrom.

In some example implementations of the control body of any preceding example implementation, or any combination of any preceding example implementations, the electrocardiogram signal or samples of the electrocardiogram signal form an identifier of the user, and the microprocessor is further configured to perform a biometric authentication of the user based on the identifier, and wherein the microprocessor further configured to control operation of the at least one functional element includes the microprocessor further configured to alter a locked state of the control body based on the biometric authentication.

In some example implementations of the control body of any preceding example implementation, or any combination of any preceding example implementations, the microprocessor further configured to perform the biometric authentication includes the microprocessor further configured to at least access a corresponding identifier of an authorized user; perform a comparison of the identifier with the corresponding identifier; and based on the comparison, verify the user is the authorized user when the identifier and the corresponding identifier match or have at least a threshold similarity.

In some example implementations of the control body of any preceding example implementation, or any combination of any preceding example implementations, the microprocessor is further configured to operate in an enrollment mode to enroll the user for biometric authentication, the microprocessor in the enrollment mode configured to receive a baseline electrocardiogram signal for the user from the heart rate monitor, and generate the corresponding identifier from the baseline electrocardiogram signal.

In some example implementations of the control body of any preceding example implementation, or any combination of any preceding example implementations, the microprocessor is further configured to force re-enrollment of the user, including the microprocessor further configured to repeat the enrollment mode in which the microprocessor is configured to receive an updated baseline electrocardiogram signal for the user, and update the corresponding identifier from the updated baseline electrocardiogram signal.

In some example implementations of the control body of any preceding example implementation, or any combination of any preceding example implementations, the microprocessor further configured to perform the biometric authentication includes the microprocessor further configured to at least access corresponding identifiers of an authorized user, the corresponding identifiers formed from respective baseline electrocardiogram signals for the authorized user; perform a comparison of the identifier with the corresponding identifiers; and based on the comparison, verify the user is the authorized user when the identifier and any of the corresponding identifiers match or have at least a threshold similarity.

In some example implementations of the control body of any preceding example implementation, or any combination of any preceding example implementations, the microprocessor is further configured to operate in an enrollment mode in which the microprocessor is configured to receive the respective baseline electrocardiogram signals from the heart rate monitor, and generate the corresponding identifiers from the respective baseline electrocardiogram signals.

In some example implementations of the control body of any preceding example implementation, or any combination of any preceding example implementations, the microprocessor further configured to perform the biometric authentication includes the microprocessor further configured to at least access corresponding identifiers of authorized users, the corresponding identifiers formed from respective baseline electrocardiogram signals for respective ones of the authorized users; perform a comparison of the identifier with the corresponding identifiers; and based on the comparison, verify the user is one of the authorized users when the identifier and any of the corresponding identifiers match or have at least a threshold similarity.

In some example implementations of the control body of any preceding example implementation, or any combination of any preceding example implementations, the microprocessor is further configured to operate in an enrollment mode in which the microprocessor is configured to receive the respective baseline electrocardiogram signals from the heart rate monitor, and generate the corresponding identifiers from the respective baseline electrocardiogram signals.

In some example implementations of the control body of any preceding example implementation, or any combination of any preceding example implementations, the control body further comprises a communication interface configured to enable communication with a computing device, wherein the microprocessor further configured to control operation of the at least one functional element includes the microprocessor further configured to cause the communication interface to communicate a notification to the computing device when the biometric authentication fails to verify the user is an authorized user.

In some example implementations of the control body of any preceding example implementation, or any combination of any preceding example implementations, the control body further comprises a communication interface configured to enable communication with an age verification system that is configured to perform an age verification of the user, wherein the microprocessor is further configured to alter the locked state of the control body based on the age verification.

These and other features, aspects, and advantages of the present disclosure will be apparent from a reading of the following detailed description together with the accompanying figures, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as combinable, unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying figures which illustrate, by way of example, the principles of some described example implementations.

BRIEF DESCRIPTION OF THE FIGURES

Figure 1:
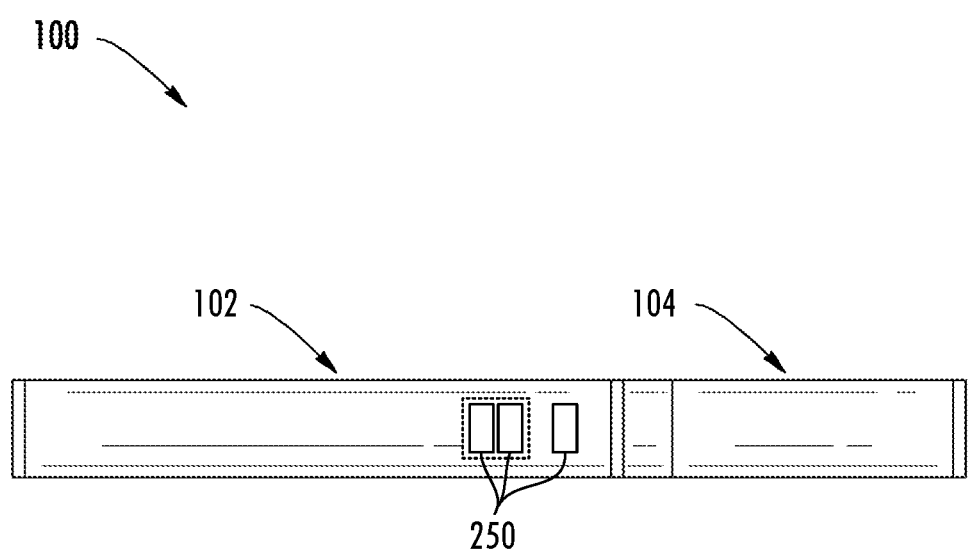
Figure 2:
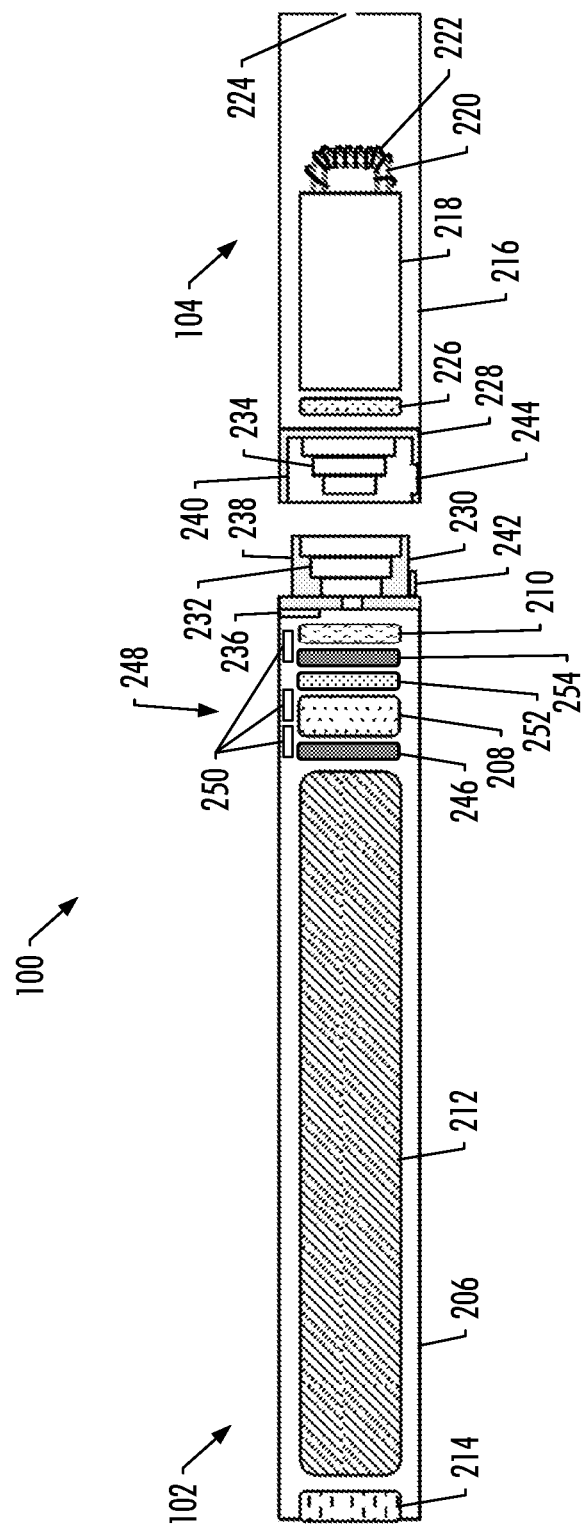

Having thus described aspects of the disclosure in the foregoing general terms, reference will now be made to the accompanying figures, which are not necessarily drawn to scale, and wherein:

FIG. 1 illustrates a side view of an aerosol delivery device including a cartridge coupled to a control body, according to an example implementation of the present disclosure;

FIG. 2 is a partially cut-away view of the aerosol delivery device according to various example implementations; and FIG. 3 illustrates a system including an aerosol delivery device in wireless communication with a computing device, according to various example implementations.

DETAILED DESCRIPTION

The present disclosure will now be described more fully hereinafter with reference to example implementations thereof. These example implementations are described so that this disclosure will be thorough and complete, and will fully convey the scope of the disclosure to those skilled in the art. Indeed, the disclosure may be embodied in many different forms and should not be construed as limited to the implementations set forth herein; rather, these implementations are provided so that this disclosure will satisfy applicable legal requirements. As used in the specification and the appended claims, unless specified otherwise or clear from context, the "or" of a set of operands is the "inclusive or" and thereby true if and only if one or more of the operands is true, as opposed to the "exclusive or" which is false when all of the operands are true. Thus, for example, "[A] or [B]" is true if [A] is true, or if [B] is true, or if both [A] and [B] are true. The singular forms "a," "an," "the" and the like include plural referents unless the context clearly dictates otherwise. Further, while reference may be made herein to quantitative measures, values, geometric relationships or the like, unless otherwise stated, any one or more if not all of these may be absolute or approximate to account for acceptable variations that may occur, such as those due to engineering tolerances or the like.

As described hereinafter, example implementations of the present disclosure relate to aerosol delivery devices. Some aerosol delivery devices according to the present disclosure use electrical energy to heat a material (preferably without combusting the material to any significant degree) to form an inhalable substance; and components of such systems have the form of articles most preferably are sufficiently compact to be considered hand-held devices. That is, use of components of preferred aerosol delivery devices does not result in the production of smoke in the sense that aerosol results principally from by-products of combustion or pyrolysis of tobacco, but rather, use of those preferred systems results in the production of vapors resulting from volatilization or vaporization of certain components incorporated therein. In some example implementations, components of aerosol delivery devices may be characterized as electronic cigarettes, and those electronic cigarettes most preferably incorporate tobacco and/or components derived from tobacco, and hence deliver tobacco derived components in aerosol form.

Aerosol generating components of certain preferred aerosol delivery devices may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol delivery device in accordance with some example implementations of the present disclosure can hold and use that component much like a smoker employs a traditional type of smoking article, draw on one end of that component for inhalation of aerosol produced by that component, take or draw puffs at selected intervals of time, and the like.

While the systems are generally described herein in terms of implementations associated with aerosol delivery devices such as so-called "e-cigarettes," "tobacco heating products" and the like, it should be understood that the mechanisms, components, features, and methods may be embodied in many different forms and associated with a variety of articles. For example, the description provided herein may be employed in conjunction with implementations of traditional smoking articles (e.g., cigarettes, cigars, pipes, etc.), heat-not-burn cigarettes, and related packaging for any of the products disclosed herein. Accordingly, it should be understood that the description of the mechanisms, components, features, and methods disclosed herein are discussed in terms of implementations relating to aerosol delivery devices by way of example only, and may be embodied and used in various other products and methods.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

In use, aerosol delivery devices of the present disclosure may be subjected to many of the physical actions employed by an individual in using a traditional type of smoking article (e.g., a cigarette, cigar or pipe that is employed by lighting and inhaling tobacco). For example, the user of an aerosol delivery device of the present disclosure can hold that article much like a traditional type of smoking article, draw on one end of that article for inhalation of aerosol produced by that article, take puffs at selected intervals of time, etc.

Aerosol delivery devices of the present disclosure generally include a number of components provided within an outer housing, which may be referred to as a body or shell. The overall design of the housing can vary, and the format or configuration of the housing that can define the overall size and shape of the aerosol delivery device can vary. Typically, an elongated body resembling the shape of a cigarette or cigar can be a formed from a single, unitary housing or the elongated housing can be formed of two or more separable bodies. For example, an aerosol delivery device can comprise an elongated housing that can be substantially tubular in shape and, as such, resemble the shape of a conventional cigarette or cigar. In one example, all of the components of the aerosol delivery device are contained within one housing. Alternatively, an aerosol delivery device can comprise two or more housings that are joined and are separable. For example, an aerosol delivery device can possess at one end a control body comprising a housing containing one or more reusable components (e.g., an accumulator such as a rechargeable battery, rechargeable supercapacitor, solid-state battery (SSB), thin-film SSB, lithium-ion or hybrid lithium-ion supercapacitor, and various electronics for controlling the operation of that article), and at the other end and removably coupleable thereto, an outer body or shell containing a disposable portion (e.g., a disposable flavor-containing cartridge). More specific formats, configurations and arrangements of components within the single housing type of unit or within a multi-piece separable housing type of unit will be evident in light of the further disclosure provided herein. Additionally, various aerosol delivery device designs and component arrangements can be appreciated upon consideration of the commercially available electronic aerosol delivery devices. It will be appreciated that alternative non-tubular housing form factors can also be used, including, for example, device housings having a shape and size generally approximating a pack of cigarettes and form factors such as used on the GLO™ by British American Tobacco and IQOS™ by Philip Morris International, Inc.

As will be discussed in more detail below, aerosol delivery devices of the present disclosure comprise some combination of a power source (i.e., an electrical power source), at least one control component (e.g., means for actuating, controlling, regulating and ceasing power for heat generation, such as by controlling electrical current flow from the power source to other components of the aerosol delivery device), a heating element (e.g., an electrical resistance heating element or other component) or vibrating piezoelectric mesh, which alone or in combination with one or more further elements may be commonly referred to as an "atomizer", an aerosol precursor composition (e.g., commonly a liquid capable of yielding an aerosol upon application of sufficient heat, such as ingredients commonly referred to as "smoke juice," "e-liquid" and "e-juice"), and a mouthend region or tip for allowing draw upon the aerosol delivery device for aerosol inhalation (e.g., a defined airflow path through the article such that aerosol generated can be withdrawn therefrom upon draw).

Alignment of the components within the aerosol delivery device of the present disclosure can vary. In specific implementations, the aerosol precursor composition can be located near an end of the aerosol delivery device which may be configured to be positioned proximal to the mouth of a user so as to maximize aerosol delivery to the user. Other configurations, however, are not excluded. Generally, the heating element can be positioned sufficiently near the aerosol precursor composition so that heat from the heating element can volatilize the aerosol precursor (as well as one or more flavorants, medicaments, or the like that may likewise be provided for delivery to a user) and form an aerosol for delivery to the user. When the heating element heats the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof, wherein such terms are also interchangeably used herein except where otherwise specified.

As noted above, the aerosol delivery device may incorporate a battery or other electrical power source to provide current flow sufficient to provide various functionalities to the aerosol delivery device, such as powering of a heater, powering of control systems, powering of indicators, and the like. The power source can take on various implementations. Preferably, the power source is able to deliver sufficient power to rapidly heat the heating element to provide for aerosol formation and power the aerosol delivery device through use for a desired duration of time. The power source preferably is sized to fit conveniently within the aerosol delivery device so that the aerosol delivery device can be easily handled. Additionally, a preferred power source is of a sufficiently light weight to not detract from a desirable smoking experience.

More specific formats, configurations and arrangements of components within the aerosol delivery devices of the present disclosure will be evident in light of the further disclosure provided hereinafter. Additionally, the selection and arrangement of various aerosol delivery device components can be appreciated upon consideration of commercially-available electronic aerosol delivery devices. Further information regarding formats, configurations and arrangements of components within the aerosol delivery devices of the present disclosure, as well as commercially-available electronic aerosol delivery devices, may be found in U.S. patent application Ser. No. 15/291,771 to Sur et al., filed Oct. 12, 2016, which is incorporated herein by reference.

FIG. 1 illustrates a side view of an aerosol delivery device 100 including a control body 102 and a cartridge 104, according to various example implementations of the present disclosure. In particular, FIG. 1 illustrates the control body and the cartridge coupled to one another. The control body and the cartridge may be detachably aligned in a functioning relationship. Various mechanisms may connect the cartridge to the control body to result in a threaded engagement, a press-fit engagement, an interference fit, a magnetic engagement or the like. The aerosol delivery device may be substantially rod-like, substantially tubular shaped, or substantially cylindrically shaped in some example implementations when the cartridge and the control body are in an assembled configuration. The aerosol delivery device may also be substantially rectangular, rhomboidal or triangular in cross-section, multifaceted shapes, or the like, some of which may lend itself to greater compatibility with a substantially flat or thin-film power source, such as a power source including a flat battery.

The control body 102 and cartridge 104 may include separate, respective housings or outer bodies, which may be formed of any of a number of different materials. The housing may be formed of any suitable, structurally-sound material. In some examples, the housing may be formed of a metal or alloy, such as stainless steel, aluminum or the like. Other suitable materials include various plastics (e.g., polycarbonate), metal-plating over plastic, ceramics and the like.

In some example implementations, one or both of the control body 102 or the cartridge 104 of the aerosol delivery device 100 may be referred to as being disposable or as being reusable. For example, the control body may have a replaceable battery, rechargeable battery (e.g., rechargeable thin-film solid state battery) or rechargeable supercapacitor, and thus may be combined with any type of recharging technology, including connection to a typical wall outlet, connection to a car charger (i.e., a cigarette lighter receptacle), connection to a computer, such as through a universal serial bus (USB) cable or connector, connection to a photovoltaic cell (sometimes referred to as a solar cell) or solar panel of solar cells, wireless connection to a Radio Frequency (RF), wireless connection to induction-based charging pads, or connection to a RF-to-DC converter. Further, in some example implementations, the cartridge may comprise a single-use cartridge, as disclosed in U.S. Pat. No. 8,910,639 to Chang et al., which is incorporated herein by reference.

FIG. 2 more particularly illustrates the aerosol delivery device 100, in accordance with some example implementations. As seen in the cut-away view illustrated therein, again, the aerosol delivery device can comprise a control body 102 and a cartridge 104 each of which include a number of respective components. The components illustrated in FIG. 2 are representative of the components that may be present in a control body and cartridge and are not intended to limit the scope of components that are encompassed by the present disclosure. As shown, for example, the control body can be formed of a control body shell 206 that can include a control component 208 (e.g., a microprocessor, individually or as part of a microcontroller), a flow sensor 210, a power source 212 and one or more light-emitting diodes (LEDs) 214, quantum dot enabled LEDs or the like, and such components can be variably aligned. The power source may include, for example, a battery (single-use or rechargeable), rechargeable supercapacitor, rechargeable solid-state battery (SSB), rechargeable lithium-ion battery (LiB) or the like, or some combination thereof. Some examples of a suitable power source are provided in U.S. patent application Ser. No. 14/918,926 to Sur et al., filed Oct. 21, 2015, which is incorporated herein by reference. Other examples of a suitable power source are provided in U.S. Pat. App. Pub. No. 2014/0283855 to Hawes et al., U.S. Pat. App. Pub. No. 2014/0014125 to Fernando et al., U.S. Pat. App. Pub. No. 2013/0243410 to Nichols et al., U.S. Pat. App. Pub. No. 2010/0313901 to Fernando et al., and U.S. Pat. App. Pub. No. 2009/0230117 to Fernando et al., all of which are incorporated herein by reference.

The LED 214 may be one example of a suitable visual indicator with which the aerosol delivery device 100 may be equipped. Other indicators such as audio indicators (e.g., speakers), haptic indicators (e.g., vibration motors) or the like can be included in addition to or as an alternative to visual indicators such as the LED, quantum dot enabled LEDs.

The cartridge 104 can be formed of a cartridge shell 216 enclosing a reservoir 218 configured to retain the aerosol precursor composition, and including a heater 222 (sometimes referred to as a heating element). In various configurations, this structure may be referred to as a tank; and accordingly, the terms "cartridge," "tank" and the like may be used interchangeably to refer to a shell or other housing enclosing a reservoir for aerosol precursor composition, and including a heater.

As shown, in some examples, the reservoir 218 may be in fluid communication with a liquid transport element 220 adapted to wick or otherwise transport an aerosol precursor composition stored in the reservoir housing to the heater 222. In some examples, a valve may be positioned between the reservoir and heater, and configured to control an amount of aerosol precursor composition passed or delivered from the reservoir to the heater.

Various examples of materials configured to produce heat when electrical current is applied therethrough may be employed to form the heater 222. The heater in these examples may be a resistive heating element such as a wire coil, micro heater or the like. Example materials from which the heating element may be formed include Kanthal (FeCrAl), Nichrome, stainless steel, Molybdenum disilicide ($MoSi_2$), molybdenum silicide (MoSi), Molybdenum disilicide doped with Aluminum ($Mo(Si,Al)_2$), graphite and graphite-based materials (e.g., carbon-based foams and yarns) and ceramics (e.g., positive or negative temperature coefficient ceramics). Example implementations of heaters or heating members useful in aerosol delivery devices according to the present disclosure are further described below, and can be incorporated into devices such as those described herein.

An opening 224 may be present in the cartridge shell 216 (e.g., at the mouthend) to allow for egress of formed aerosol from the cartridge 104.

The cartridge 104 also may include one or more electronic components 226, which may include an integrated circuit, a memory component (e.g., EEPROM, flash memory), a sensor, or the like. The electronic components may be adapted to communicate with the control component 208 and/or with an external device by wired or wireless means. The electronic components may be positioned anywhere within the cartridge or a base 228 thereof.

Although the control component 208 and the flow sensor 210 are illustrated separately, it is understood that various electronic components including the control component and the flow sensor may be combined on an electronic printed circuit board (PCB) that supports and electrically connects the electronic components. Further, the PCB may be positioned horizontally relative the illustration of FIG. 1 in that the PCB can be lengthwise parallel to the central axis of the control body. In some examples, the air flow sensor may comprise its own PCB or other base element to which it can be attached. In some examples, a flexible PCB may be utilized. A flexible PCB may be configured into a variety of shapes, include substantially tubular shapes. In some examples, a flexible PCB may be combined with, layered onto, or form part or all of a heater substrate.

The control body 102 and the cartridge 104 may include components adapted to facilitate a fluid engagement therebetween. As illustrated in FIG. 2, the control body can include a coupler 230 having a cavity 232 therein. The base 228 of the cartridge can be adapted to engage the coupler and can include a projection 234 adapted to fit within the cavity. Such engagement can facilitate a stable connection between the control body and the cartridge as well as establish an electrical connection between the power source 212 and control component 208 in the control body and the heater 222 in the cartridge. Further, the control body shell 206 can include an air intake 236, which may be a notch in the shell where it connects to the coupler that allows for passage of ambient air around the coupler and into the shell where it then passes through the cavity 232 of the coupler and into the cartridge through the projection 234.

A coupler and a base useful according to the present disclosure are described in U.S. Pat. App. Pub. No. 2014/0261495 to Novak et al., which is incorporated herein by reference. For example, the coupler 230 as seen in FIG. 2 may define an outer periphery 238 configured to mate with an inner periphery 240 of the base 228. In one example the inner periphery of the base may define a radius that is substantially equal to, or slightly greater than, a radius of the outer periphery of the coupler. Further, the coupler may define one or more protrusions 242 at the outer periphery configured to engage one or more recesses 244 defined at the inner periphery of the base. However, various other examples of structures, shapes and components may be employed to couple the base to the coupler. In some examples the connection between the base of the cartridge 104 and the coupler of the control body 102 may be substantially permanent, whereas in other examples the connection therebetween may be releasable such that, for example, the control body may be reused with one or more additional cartridges that may be disposable and/or refillable.

The reservoir 218 illustrated in FIG. 2 can be a container or can be a fibrous reservoir, as presently described. For example, the reservoir can comprise one or more layers of nonwoven fibers substantially formed into the shape of a tube encircling the interior of the cartridge shell 216, in this example. An aerosol precursor composition can be retained in the reservoir. Liquid components, for example, can be sorptively retained by the reservoir. The reservoir can be in fluid connection with the liquid transport element 220. The liquid transport element can transport the aerosol precursor composition stored in the reservoir via capillary action to the heater 222 that is in the form of a metal wire coil in this example. As such, the heater is in a heating arrangement with the liquid transport element.

In some examples, a microfluidic chip may be embedded in the reservoir 218, and the amount and/or mass of aerosol precursor composition delivered from the reservoir may be controlled by a micro pump, such as one based on microelectromechanical systems (MEMS) technology. The heater 222 may be configured to implement radio-frequency inductive based heating of the aerosol precursor composition without a wick or physical contact with the aerosol precursor composition, such as in a manner described in U.S. patent application Ser. No. 14/934,763 to Davis et al., filed Nov. 6, 2015, which is incorporated by reference. Other example implementations of reservoirs and transport elements useful in aerosol delivery devices according to the present disclosure are further described below, and such reservoirs and/or transport elements can be incorporated into devices such as those described herein. In particular, specific combinations of heating members and transport elements as further described below may be incorporated into devices such as those described herein.

In use, when a user draws on the aerosol delivery device 100, airflow is detected by the flow sensor 210, and the heater 222 is activated to vaporize components of the aerosol precursor composition. Drawing upon the mouthend of the aerosol delivery device causes ambient air to enter the air intake 236 and pass through the cavity 232 in the coupler 230 and the central opening in the projection 234 of the base 228. In the cartridge 104, the drawn air combines with the formed vapor to form an aerosol. The aerosol is whisked, aspirated or otherwise drawn away from the heater and out the opening 224 in the mouthend of the aerosol delivery device.

In some examples, the aerosol delivery device 100 may include a number of additional software-controlled functions. For example, the aerosol delivery device may include a power-source protection circuit configured to detect power-source input, loads on the power-source terminals, and charging input. The power-source protection circuit may include short-circuit protection, under-voltage lock out and/or over-voltage charge protection, battery temperature compensation. The aerosol delivery device may also include components for ambient temperature measurement, and its control component 208 may be configured to control at least one functional element to inhibit power-source charging— particularly of any battery—if the ambient temperature is below a certain temperature (e.g., 0° C.) or above a certain temperature (e.g., 45° C.) prior to start of charging or during charging.

Additionally or alternatively, in some examples, the control component 208 may include a microprocessor with an embedded analog-to-digital converter (ADC) useful for measurement of the temperature of the heater 222. More particularly, for example, the microprocessor may be programmed to cause a fixed current to the heater, and measure the voltage across the heater. The microprocessor may then be configured to calculate the resistance of the heater that varies with temperature from the current and voltage (R=V/I). The resistance may then be used to determine the temperature of the heater from a known relationship between resistance and temperature for the heater material. This relationship may be expressed in a number of different manners, such as by a lookup table.

Power delivery from the power source 212 may vary over the course of each puff on the device 100 according to a power control mechanism. The device may include a "long puff" safety timer such that in the event that a user or component failure (e.g., flow sensor 210) causes the device to attempt to puff continuously, the control component 208 may control at least one functional element to terminate the puff automatically after some period of time (e.g., four seconds). Further, the time between puffs on the device may be restricted to less than a period of time (e.g., 100 seconds). A watchdog safety timer may automatically reset the aerosol delivery device if its control component or software running on it becomes unstable and does not service the timer within an appropriate time interval (e.g., eight seconds). Further safety protection may be provided in the event of a defective or otherwise failed flow sensor 210, such as by permanently disabling the aerosol delivery device in order to prevent inadvertent heating. A puffing limit switch may deactivate the device in the event of a pressure sensor fail causing the device to continuously activate without stopping after the four second maximum puff time.

The aerosol delivery device 100 may include a puff tracking algorithm configured for heater lockout once a defined number of puffs has been achieved for an attached cartridge (based on the number of available puffs calculated in light of the e-liquid charge in the cartridge). The aerosol delivery device may include a sleep, standby or low-power mode function whereby power delivery may be automatically cut off after a defined period of non-use. Further safety protection may be provided in that all charge/discharge cycles of the power source 212 may be monitored by the control component 208 over its lifetime. After the power source has attained the equivalent of a predetermined number (e.g., 200) of full discharge and full recharge cycles, it may be declared depleted, and the control component may control at least one functional element to prevent further charging of the power source.

The various components of an aerosol delivery device according to the present disclosure can be chosen from components described in the art and commercially available. Examples of batteries that can be used according to the disclosure are described in U.S. Pat. No. 9,484,155 to Peckerar et al., which is incorporated herein by reference.

The aerosol delivery device 100 can incorporate the sensor 210 or another sensor or detector for control of supply of electric power to the heater 222 when aerosol generation is desired (e.g., upon draw during use). As such, for example, there is provided a manner or method of turning off power to the heater when the aerosol delivery device is not being drawn upon during use, and for turning on power to actuate or trigger the generation of heat by the heater during draw. Additional representative types of sensing or detection mechanisms, structure and configuration thereof, components thereof, and general methods of operation thereof, are described in U.S. Pat. No. 5,261,424 to Sprinkel, Jr., U.S. Pat. No. 5,372,148 to McCafferty et al., and PCT Pat. App. Pub. No. WO 2010/003480 to Flick, all of which are incorporated herein by reference.

The aerosol delivery device 100 most preferably incorporates the control component 208 or another control mechanism for controlling the amount of electric power to the heater 222 during draw. Representative types of electronic components, structure and configuration thereof, features thereof, and general methods of operation thereof, are described in U.S. Pat. No. 4,735,217 to Gerth et al., U.S. Pat. No. 4,947,874 to Brooks et al., U.S. Pat. No. 5,372,148 to McCafferty et al., U.S. Pat. No. 6,040,560 to Fleischhauer et al., U.S. Pat. No. 7,040,314 to Nguyen et al., U.S. Pat. No. 8,205,622 to Pan, U.S. Pat. No. 8,881,737 to Collet et al., U.S. Pat. No. 9,423,152 to Ampolini et al., U.S. Pat. No. 9,439,454 to Fernando et al., and U.S. Pat. App. Pub. No. 2015/0257445 to Henry et al., all of which are incorporated herein by reference.

Representative types of substrates, reservoirs or other components for supporting the aerosol precursor are described in U.S. Pat. No. 8,528,569 to Newton, U.S. Pat. App. Pub. No. 2014/0261487 to Chapman et al., U.S. Pat. App. Pub. No. 2015/0059780 to Davis et al., and U.S. Pat. App. Pub. No. 2015/0216232 to Bless et al., all of which are incorporated herein by reference. Additionally, various wicking materials, and the configuration and operation of those wicking materials within certain types of electronic cigarettes, are set forth in U.S. Pat. No. 8,910,640 to Sears et al., which is incorporated herein by reference.

The aerosol precursor composition, also referred to as a vapor precursor composition, may comprise a variety of components including, by way of example, a polyhydric alcohol (e.g., glycerin, propylene glycol or a mixture thereof), nicotine, tobacco, tobacco extract and/or flavorants. Representative types of aerosol precursor components and formulations also are set forth and characterized in U.S. Pat. No. 7,217,320 to Robinson et al., U.S. Pat. No. 9,254,002 to Chong et al., U.S. Pat. No. 8,881,737 to Collett et al., U.S. Pat. Pub. No. 2013/0008457 to Zheng et al., U.S. Pat. Pub. No. 2015/0020823 to Lipowicz et al., and U.S. Pat. Pub. No. 2015/0020830 to Koller, as well as PCT Pat. App. Pub. No. WO 2014/182736 to Bowen et al., and U.S. patent application Ser. No. 15/222,615 to Watson et al., filed Jul. 28, 2016, the disclosures of which are incorporated herein by reference. Other aerosol precursors that may be employed include the aerosol precursors that have been incorporated in the VUSE® product by R. J. Reynolds Vapor Company, the BLU™ product by Imperial Tobacco Group PLC, the MISTIC MENTHOL product by Mistic Ecigs, and the VYPE product by CN Creative Ltd. Also desirable are the so-called "smoke juices" for electronic cigarettes that have been available from Johnson Creek Enterprises LLC.

Implementations of effervescent materials can be used with the aerosol precursor, and are described, by way of example, in U.S. Pat. App. Pub. No. 2012/0055494 to Hunt et al., which is incorporated herein by reference. Further, the use of effervescent materials is described, for example, in U.S. Pat. No. 4,639,368 to Niazi et al., U.S. Pat. No. 5,178,878 to Wehling et al., U.S. Pat. No. 5,223,264 to Wehling et al., U.S. Pat. No. 6,974,590 to Pather et al., U.S. Pat. No. 7,381,667 to Bergquist et al., U.S. Pat. No. 8,424,541 to Crawford et al., and U.S. Pat. No. 8,627,828 to Strickland et al., as well as U.S. Pat. No. 9,307,787 to Sun et al., U.S. Pat. App. Pub. No. 2010/0018539 to Brinkley et al., and PCT Pat. App. Pub. No. WO 97/06786 to Johnson et al., all of which are incorporated by reference herein. Additional description with respect to implementations of aerosol precursor compositions, including description of tobacco or components derived from tobacco included therein, is provided in U.S. patent application Ser. Nos. 15/216,582 and 15/216,590, each filed Jul. 21, 2016 and each to Davis et al., which are incorporated herein by reference.

Additional representative types of components that yield visual cues or indicators may be employed in the aerosol delivery device 100, such as visual indicators and related components, audio indicators, haptic indicators and the like. Examples of suitable LED components, and the configurations and uses thereof, are described in U.S. Pat. No. 5,154,192 to Sprinkel et al., U.S. Pat. No. 8,499,766 to Newton, U.S. Pat. No. 8,539,959 to Scatterday, and U.S. Pat. No. 9,451,791 to Sears et al., all of which are incorporated herein by reference.

Yet other features, controls or components that can be incorporated into aerosol delivery devices of the present disclosure are described in U.S. Pat. No. 5,967,148 to Harris et al., U.S. Pat. No. 5,934,289 to Watkins et al., U.S. Pat. No. 5,954,979 to Counts et al., U.S. Pat. No. 6,040,560 to Fleischhauer et al., U.S. Pat. No. 8,365,742 to Hon, U.S. Pat. No. 8,402,976 to Fernando et al., U.S. Pat. App. Pub. No. 2005/0016550 to Katase, U.S. Pat. No. 8,689,804 to Fernando et al., U.S. Pat. App. Pub. No. 2013/0192623 to Tucker et al., U.S. Pat. No. 9,427,022 to Leven et al., U.S. Pat. App. Pub. No. 2013/0180553 to Kim et al., U.S. Pat. App. Pub. No. 2014/0000638 to Sebastian et al., U.S. Pat. App. Pub. No. 2014/0261495 to Novak et al., and U.S. Pat. No. 9,220,302 to DePiano et al., all of which are incorporated herein by reference.

As indicated above, the control component 208 includes a number of electronic components, and in some examples may be formed of a PCB. The electronic components may include a microprocessor or processor core, and a memory. In some examples, the control component may include a microcontroller with integrated processor core and memory, and may further include one or more integrated input/output peripherals. In some examples, the control component may be coupled to a communication interface 246 to enable (wired or wireless) communication with one or more networks, computing devices or other appropriately-enabled devices. Examples of suitable communication interfaces are disclosed in U.S. Pat. App. Pub. No. 2016/0261020 to Marion et al., the content of which is incorporated herein by reference. Another example of a suitable communication interface is the CC3200 single chip wireless microcontroller unit (MCU) from Texas Instruments. And examples of suitable manners according to which the aerosol delivery device may be configured to wirelessly communicate are disclosed in U.S. Pat. App. Pub. No. 2016/0007651 to Ampolini et al., and U.S. Pat. App. Pub. No. 2016/0219933 to Henry, Jr. et al., each of which is incorporated herein by reference.

As further shown in FIGS. 1 and 2, in accordance with some example implementations, the control body 102 includes a heart rate monitor 248 including a plurality of biopotential electrodes 250 affixed to the shell 206 (housing) and configured to obtain biopotential measurements from a user. This may include, for example, two or three biopotential electrodes that obtain biopotential measurements from a user who contacts the biopotential electrodes with their hands. The biopotential electrodes may be any of a number of different types of electrodes capable of obtaining biopotential measurements that represent activity of the heart, which manifests its function through electric activity.

The heart rate monitor 248 also includes signal conditioning circuitry 252 configured to produce an electrocardiogram signal from the biopotential measurements. One example of suitable signal conditioning circuitry is implemented in an integrated circuit (IC) such as the model AD8233 heart rate monitor from Analog Devices.

In some examples, the control component 208 (microprocessor) is coupled to the signal conditioning circuitry 252 and further configured to control operation of at least one functional element of the control body 102 or the aerosol delivery device 100 based on the electrocardiogram signal or a heart rate of the user calculated therefrom. This may include the control component being configured to calculate the heart rate of the user from the electrocardiogram signal, and control operation of the functional element(s) based on the heart rate so calculated. The heart rate may be calculated in any suitable manner and expressed in beats per minute (bpm).

Functional element(s) of the control body 102 or the aerosol delivery device 100 may be controlled in any of a number of different manners in based on the electrocardiogram signal or heart rate. For example, an indicator 254 (e.g., visual indicator, audio indicator, haptic indicator) may be controlled to provide a user-perceptible feedback (e.g., visual, audible, haptic feedback). The feedback may include, for example, a visual readout of the electrocardiogram signal or heart rate. Additionally or alternatively, for example, the feedback may include a visual, audible and/or haptic notification that the heart rate is above or below a predefined threshold, or within or outside a predefined range. In these instances, the indicator may provide the user-perceptible feedback such as an alarm, buzzer, vibration or visual indicator (e.g., LED).

Additionally or alternatively, in some examples, the electrocardiogram signal or heart rate may be used for biometric authentication of the user. In these examples, the electrocardiogram signal or samples of the electrocardiogram signal may form an identifier of the user. In the context of electrocardiography, for example, the identifier may be or include a series of calculated intervals, axis, or other measurable parameters such as the PR interval, QT interval, PR axis, and QRS axis.

In these examples, the control component 208 may be further configured to perform a biometric authentication of the user based on the identifier. The control component may then be configured to control operation of at least one functional element of the aerosol delivery device 100 or the control body 102 based on the biometric authentication, such as to alter a locked state of the aerosol delivery device or its control body. In this regard, the aerosol delivery device or its control body may be locked whereby the device/control body or more specifically one or more of its components (e.g., atomizer) may be disabled, and the control component may unlock the device/control body when the user is authenticated.

The biometric authentication may be performed in a number of different manners. For example, the control component 208 may be configured to access a corresponding identifier of an authorized user, such as from memory onboard the control component or more generally the aerosol delivery device 100. The control component may be configured to perform a comparison of the identifier with the corresponding identifier, and based on the comparison, verify the user is the authorized user when the identifier and the corresponding identifier match or have at least a threshold similarity. In some examples, the control component may then unlock the aerosol delivery device 100 or its control body 102 when the user is verified as the authorized user.

In some examples, the aerosol delivery device 100, or more particularly its control body 102, may accommodate multiple authorized users. Additionally or alternatively, there may be multiple corresponding identifiers of an authorized user, which may represent electrocardiogram signals for the authorized user exposed to different stressors. It will be appreciated that the electrocardiogram signal represents electrical activity of the heart; and accordingly, the electrocardiogram signal (or more particularly a pattern of the electrocardiogram signal) may change with various stressors that cause stress to the user. One example of a stressor is physical activity such as exercise that can cause an increased heart rate.

In some examples in which there are multiple authorized users, the control component 208 may be configured to access corresponding identifiers of the authorized users, perform a comparison of the identifier with the corresponding identifiers, and verify the user is one of the authorized users when the identifier and any of the corresponding identifiers match or have at least a threshold similarity. Similarly, in some examples in which there are multiple corresponding identifiers of the authorized user, the control component may be configured to access the corresponding identifiers of the authorized, perform a similar comparison, verify the user is the authorized user when the identifier and any of the corresponding identifiers match or have at least a threshold similarity.

To enable biometric authentication, the control component 208 may be further configured to operate in an enrollment mode to enroll the user for biometric authentication. In this mode, the biopotential electrodes 250 of the heart rate monitor 248 may obtain biopotential measurements from the user, over a period of time such as thirty seconds. The signal conditioning circuitry 252 may produce a baseline electrocardiogram signal from the biopotential measurements. The control component, then, may be configured to receive the baseline electrocardiogram signal for the user from the heart rate monitor, and generate the corresponding identifier from the baseline electrocardiogram signal.

In some examples, the control component 208 may be further configured to re-enroll the user. This may include the control component configured to repeat the enrollment mode in which the control component is configured to receive an updated baseline electrocardiogram signal for the user, and update the corresponding identifier from the updated baseline electrocardiogram signal. This re-enrollment may be repeated on-demand, or the control component may be configured to force re-enrollment of the user, such as periodically at regularly or irregularly occurring intervals. In some particular examples, the control component may force re-enrollment weekly, monthly or annually. Additionally or alternatively, for example, re-enrollment may be forced each time the control body 102 is coupled with a cartridge 104. In some further examples, the control component may erase the corresponding identifier from the aerosol delivery device 100, and thereby require re-enrollment for biometric authentication. This may be triggered on-demand, automatically regularly or irregularly occurring intervals, or automatically if the aerosol delivery device is left dormant for a certain period of time.

When the biometric authentication fails to verify the user is an authorized user, the control component 208 may respond in any of a number of different manners. The control component may repeat the biometric authentication to reattempt to verify the user. The control component may be set to allow a certain number of repeated attempts before requiring a different type of authentication to unlock the aerosol delivery device 100. Additionally or alternatively, in some examples, the control component may communicate a notification to a computing device, which may be associated with a registered owner of the aerosol delivery device, as further described below.

Figure 3:
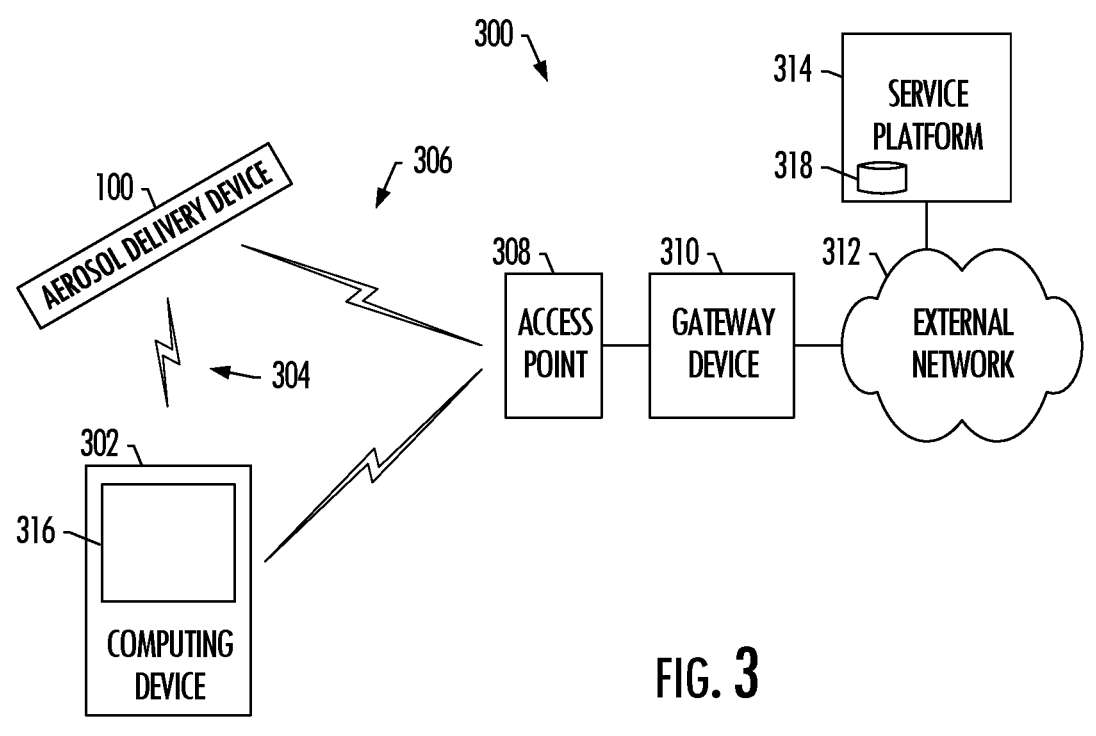

FIG. 3 illustrates a system 300 including an aerosol delivery device 100 in wireless communication with a computing device 302 external to the aerosol delivery device (an external computing device). This computing device may also be embodied as a number of different devices, such as any of a number of different mobile computers. More particular examples of suitable mobile computers include portable computers (e.g., laptops, notebooks, tablet computers), mobile phones (e.g., cell phones, smartphones), wearable computers (e.g., smartwatches) and the like. In other examples, the computing device may be embodied as other than a mobile computer, such as in the manner of a desktop computer, server computer or the like.

In some examples, the communication interface 246 of the aerosol delivery device 100 is configured to enable establishment of or connection to a wireless personal area network (WPAN) 304 that includes the computing device 302. Examples of suitable WPAN technologies include those based on or specified by IEEE 802.15 standards, including Bluetooth, Bluetooth low energy (Bluetooth LE), ZigBee, infrared (e.g., IrDA), radio-frequency identification (RFID), Wireless USB and the like. Other examples of suitable WPAN technologies include Wi-Fi Direct, as well as certain other technologies based on or specified by IEEE 802.11 standards and that support direct device-to-device communication.

In some examples, the communication interface 246 of the aerosol delivery device 100 is configured to enable connection to a wireless local area network (WLAN) 306. Examples of suitable WLAN technologies include those based on or specified by IEEE 802.11 standards and marketed as Wi-Fi. The WLAN includes appropriate networking hardware, some of which may be integral and others of which may be separate and interconnected. As shown, for example, the WLAN includes a wireless access point 308 configured to permit wireless devices including the aerosol delivery device 100 and computing device 302 to connect to the WLAN. As also shown, for example, the WLAN may include a gateway device 310 such as a residential gateway configured to connect the WLAN to an external computer network 312 such as a wide area network (WAN) like the Internet. In some examples, the wireless access point or gateway device may include an integrated router to which other systems or devices may be connected. The WLAN may also include other integral or separate and connected networking hardware, such as a network switch, hub, digital subscriber line (DSL) modem, cable modem or the like.

In some examples, the system 300 further includes a service platform 314, which may be embodied as a computer system accessible by the WLAN 306 or external network 312 (as shown). The service platform may include one or more servers, such as may be provided by one or more blade servers, a cloud computing infrastructure or the like. In some examples, the service platform is embodied as a distributed computing apparatus including multiple computing devices, such as may be used to provide a cloud computing infrastructure. And in these examples, the computing devices that form the service platform may be in communication with each other via a network such as the external network.

In some examples, the service platform 314 is accessible by the aerosol delivery device 100 over the WLAN 306 and external network 312, and configured to provide one or more services for a user of the aerosol delivery device and perhaps the users of other aerosol delivery devices. For example, the service platform may be operated by a medical professional, a health, activity or fitness tracking company or organization, or the like. The service platform may enable a user to access and use various features, such as features for monitoring or tracking the electrocardiogram signal and/or heart rate of the user of the aerosol delivery device.

Similar to the aerosol delivery device 100, in some examples, the service platform 314 is accessible by the computing device 302 over the WLAN 306 and external network 312, although the WLAN or external network may be different between the aerosol delivery device and computing device. The computing device may include or otherwise provide an installed application or other interface through which the service platform may be accessible. This application or other interface may be or may be provided by a thin client and/or other client application, such as a web browser application through which a web page (e.g., service portal) provided by the service platform may be accessible. As another example, the application or other interface may be or may be provided by a dedicated application, such as a mobile app installed on a computing device embodied as a mobile computing device.

In some examples, then, the control component 208 is configured to cause the communication interface 246 to wirelessly communicate the electrocardiogram signal or heart rate to the computing device 302 and/or service platform 314 configured to control operation of at least one of their respective functional elements based on the electrocardiogram signal or heart rate. In more particular examples, the communication interface may be caused to wirelessly communicate the electrocardiogram signal. In these examples, the computing device and/or service platform may calculate the heart rate of the user from the electrocardiogram signal, and control operation of their respective functional element(s) based on the heart rate so calculated.

Similar to the aerosol delivery device 100, functional element(s) of the computing device 302 and/or service platform 314 may be controlled in any of a number of different manners in based on the electrocardiogram signal or heart rate. For example, the computing device may control an indicator 316 (e.g., visual indicator, audio indicator, haptic indicator) to provide a user-perceptible feedback (e.g., visual, audible, haptic feedback), such as a visual readout of the electrocardiogram signal or heart rate, and/or a visual, audible and/or haptic notification that the heart rate is above or below a predefined threshold, or within or outside a predefined range. In another example, the service platform may include a database 318 controlled to store the electrocardiogram signal and/or heart rate for later retrieval, analysis and/or display, such as by the user and/or a medical professional authorized for access by the user. This may also trigger other actions, such as dispatch of an ambulance or a call to an emergency contact in instances in which the heart rate is above or below a predefined threshold.

In some examples in which the electrocardiogram signal or heart rate is used for biometric authentication of the user, the control component 208 may be configured to cause the communication interface 246 to communicate a notification to the computing device 302 (directly or via the service platform 314) when the biometric authentication fails to verify the user is an authorized user. Examples of suitable notifications include a push notification, text message or the like, which may be presented as user-perceptible feedback by the indicator 316.

Additionally or alternatively, the computing device 302 may be configured to remotely control the aerosol delivery device 100 (directly or via the service platform 314). For example, the computing device may remotely control the aerosol delivery device to lock, or otherwise remotely lock the aerosol delivery device. In another example, the computing device may remotely cause the aerosol delivery device to provide a user-perceptible feedback (e.g., visual, audible, haptic feedback), which may allow the user to locate their aerosol delivery device.

In some examples, the system 300 further includes an age verification system, which may be provided by the service platform 314 or another service platform. In some of these examples, the communication interface 246 of the aerosol delivery device 100 may enable communication with the with the age verification system. The age verification system may be configured to perform an age verification of the user, and the control component 208 may be configured to alter the locked state of the aerosol delivery device or its control body 102 based on the age verification. Similar to before, the aerosol delivery device or its control body may be locked whereby the device/control body or more specifically one or more of its components (e.g., atomizer) may be disabled, and the control component may unlock the device/control body when the age of the user is verified. This may be in addition to or in lieu of the biometric authentication described above. More information regarding suitable techniques according to which the age verification may be performed may be found in U.S. patent application Ser. No. 16/415,444 to Daugherty et al., U.S. patent application Ser. No. 16/415,460 to Hubbard et al., and U.S. patent application Ser. No. 16/415,477 to Hubbard et al., all filed May 17, 2019, all of which are incorporated herein by reference. Suitable techniques according to which the age verification may be performed may also be found in U.S. patent application Ser. No. 16/441,903 to Hubbard et al., and U.S. patent application Ser. No. 16/441,937 to Hubbard et al., both filed Jun. 14, 2019, both of which are also incorporated herein by reference.

The foregoing description of use of the article(s) can be applied to the various example implementations described herein through minor modifications, which can be apparent to the person of skill in the art in light of the further disclosure provided herein. The above description of use, however, is not intended to limit the use of the article but is provided to comply with all necessary requirements of disclosure of the present disclosure. Any of the elements shown in the article(s) illustrated in FIGS. 1-5 or as otherwise described above may be included in an aerosol delivery device according to the present disclosure.

Many modifications and other implementations of the disclosure set forth herein will come to mind to one skilled in the art to which this disclosure pertains having the benefit of the teachings presented in the foregoing descriptions and the associated figures. Therefore, it is to be understood that the disclosure is not to be limited to the specific implementations disclosed, and that modifications and other implementations are intended to be included within the scope of the appended claims. Moreover, although the foregoing descriptions and the associated figures describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. An aerosol delivery device comprising:
   at least one housing structured to retain an aerosol precursor composition;
   an atomizer;
   a microprocessor configured to operate in an active mode in which the control body is configured to control the atomizer to activate and produce an aerosol from the aerosol precursor composition; and
   a heart rate monitor including a plurality of biopotential electrodes affixed to the housing and configured to obtain biopotential measurements from a user, and including signal conditioning circuitry configured to produce an electrocardiogram signal from the biopotential measurements,
   wherein the microprocessor is coupled to the signal conditioning circuitry and further configured to control operation of at least one functional element of the aerosol delivery device based on the electrocardiogram signal or a heart rate of the user calculated therefrom.

2. The aerosol delivery device of claim 1, wherein the electrocardiogram signal or samples of the electrocardiogram signal form an identifier of the user, and the microprocessor is further configured to perform a biometric authentication of the user based on the identifier, and
   wherein the microprocessor further configured to control operation of the at least one functional element includes the microprocessor further configured to alter a locked state of the aerosol delivery device based on the biometric authentication.

3. The aerosol delivery device of claim 2, wherein the microprocessor further configured to perform the biometric authentication includes the microprocessor further configured to at least:
   access a corresponding identifier of an authorized user;
   perform a comparison of the identifier with the corresponding identifier; and based on the comparison,
   verify the user is the authorized user when the identifier and the corresponding identifier match or have at least a threshold similarity.

4. The aerosol delivery device of claim 3, wherein the microprocessor is further configured to operate in an enrollment mode to enroll the user for biometric authentication, the microprocessor in the enrollment mode configured to receive a baseline electrocardiogram signal for the user from the heart rate monitor, and generate the corresponding identifier from the baseline electrocardiogram signal.

5. The aerosol delivery device of claim 4, wherein the microprocessor is further configured to force re-enrollment of the user, including the microprocessor further configured to repeat the enrollment mode in which the microprocessor is configured to receive an updated baseline electrocardiogram signal for the user, and update the corresponding identifier from the updated baseline electrocardiogram signal.

6. The aerosol delivery device of claim 2, wherein the microprocessor further configured to perform the biometric authentication includes the microprocessor further configured to at least:
   access corresponding identifiers of an authorized user, the corresponding identifiers formed from respective baseline electrocardiogram signals for the authorized user;
   perform a comparison of the identifier with the corresponding identifiers; and based on the comparison,
   verify the user is the authorized user when the identifier and any of the corresponding identifiers match or have at least a threshold similarity.

7. The aerosol delivery device of claim 6, wherein the microprocessor is further configured to operate in an enrollment mode in which the microprocessor is configured to receive the respective baseline electrocardiogram signals from the heart rate monitor, and generate the corresponding identifiers from the respective baseline electrocardiogram signals.

8. The aerosol delivery device of claim 2, wherein the microprocessor further configured to perform the biometric authentication includes the microprocessor further configured to at least:
   access corresponding identifiers of authorized users, the corresponding identifiers formed from respective baseline electrocardiogram signals for respective ones of the authorized users;
   perform a comparison of the identifier with the corresponding identifiers; and based on the comparison,
   verify the user is one of the authorized users when the identifier and any of the corresponding identifiers match or have at least a threshold similarity.

9. The aerosol delivery device of claim 8, wherein the microprocessor is further configured to operate in an enrollment mode in which the microprocessor is configured to receive the respective baseline electrocardiogram signals from the heart rate monitor, and generate the corresponding identifiers from the respective baseline electrocardiogram signals.

10. The aerosol delivery device of claim 2 further comprising a communication interface configured to enable communication with a computing device,
    wherein the microprocessor further configured to control operation of the at least one functional element includes the microprocessor further configured to cause the communication interface to communicate a notification to the computing device when the biometric authentication fails to verify the user is an authorized user.

11. The aerosol delivery device of claim 2 further comprising a communication interface configured to enable communication with an age verification system that is configured to perform an age verification of the user,
    wherein the microprocessor is further configured to alter the locked state of the aerosol delivery device based on the age verification.

12. A control body for an aerosol delivery device, the control body comprising:
    a housing;
    a microprocessor configured to operate in an active mode in which the microprocessor is configured to control an atomizer to activate and produce an aerosol from an aerosol precursor composition; and
    a heart rate monitor including a plurality of biopotential electrodes affixed to the housing and configured to obtain biopotential measurements from a user, and including signal conditioning circuitry configured to produce an electrocardiogram signal from the biopotential measurements,
    wherein the microprocessor is coupled to the signal conditioning circuitry and further configured to control operation of at least one functional element of the control body or the aerosol delivery device based on the electrocardiogram signal or a heart rate of the user calculated therefrom.

13. The control body of claim 12, wherein the electrocardiogram signal or samples of the electrocardiogram signal form an identifier of the user, and the microprocessor is further configured to perform a biometric authentication of the user based on the identifier, and wherein the microprocessor further configured to control operation of the at least one functional element includes the microprocessor further configured to alter a locked state of the control body based on the biometric authentication.

14. The control body of claim 13, wherein the microprocessor further configured to perform the biometric authentication includes the microprocessor further configured to at least:

access a corresponding identifier of an authorized user;
perform a comparison of the identifier with the corresponding identifier; and based on the comparison,
verify the user is the authorized user when the identifier and the corresponding identifier match or have at least a threshold similarity.

15. The control body of claim 14, wherein the microprocessor is further configured to operate in an enrollment mode to enroll the user for biometric authentication, the microprocessor in the enrollment mode configured to receive a baseline electrocardiogram signal for the user from the heart rate monitor, and generate the corresponding identifier from the baseline electrocardiogram signal.

16. The control body of claim 15, wherein the microprocessor is further configured to force re-enrollment of the user, including the microprocessor further configured to repeat the enrollment mode in which the microprocessor is configured to receive an updated baseline electrocardiogram signal for the user, and update the corresponding identifier from the updated baseline electrocardiogram signal.

17. The control body of claim 13, wherein the microprocessor further configured to perform the biometric authentication includes the microprocessor further configured to at least:

access corresponding identifiers of an authorized user, the corresponding identifiers formed from respective baseline electrocardiogram signals for the authorized user;
perform a comparison of the identifier with the corresponding identifiers; and based on the comparison,
verify the user is the authorized user when the identifier and any of the corresponding identifiers match or have at least a threshold similarity.

18. The control body of claim 17, wherein the microprocessor is further configured to operate in an enrollment mode in which the microprocessor is configured to receive the respective baseline electrocardiogram signals from the heart rate monitor, and generate the corresponding identifiers from the respective baseline electrocardiogram signals.

19. The control body of claim 13, wherein the microprocessor further configured to perform the biometric authentication includes the microprocessor further configured to at least:

access corresponding identifiers of authorized users, the corresponding identifiers formed from respective baseline electrocardiogram signals for respective ones of the authorized users;
perform a comparison of the identifier with the corresponding identifiers; and based on the comparison,
verify the user is one of the authorized users when the identifier and any of the corresponding identifiers match or have at least a threshold similarity.

20. The control body of claim 19, wherein the microprocessor is further configured to operate in an enrollment mode in which the microprocessor is configured to receive the respective baseline electrocardiogram signals from the heart rate monitor, and generate the corresponding identifiers from the respective baseline electrocardiogram signals.

21. The control body of claim 13 further comprising a communication interface configured to enable communication with a computing device, wherein the microprocessor further configured to control operation of the at least one functional element includes the microprocessor further configured to cause the communication interface to communicate a notification to the computing device when the biometric authentication fails to verify the user is an authorized user.

22. The control body of claim 13 further comprising a communication interface configured to enable communication with an age verification system that is configured to perform an age verification of the user, wherein the microprocessor is further configured to alter the locked state of the control body based on the age verification.

* * * * *